(12) United States Patent
Makarov et al.

(10) Patent No.: US 10,090,140 B2
(45) Date of Patent: Oct. 2, 2018

(54) IRMS SAMPLE INTRODUCTION SYSTEM AND METHOD

(71) Applicant: Thermo Fisher Scientific (Bremen) GmbH, Bremen (DE)

(72) Inventors: Alexander A. Makarov, Bremen (DE); Stevan R. Horning, Delmenhorst (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/402,108

(22) Filed: Jan. 9, 2017

(65) Prior Publication Data
US 2017/0200596 A1 Jul. 13, 2017

(30) Foreign Application Priority Data
Jan. 12, 2016 (GB) .................................. 1600569.6

(51) Int. Cl.
*H01J 49/04* (2006.01)
*G01N 15/02* (2006.01)

(52) U.S. Cl.
CPC ........ *H01J 49/0422* (2013.01); *H01J 49/044* (2013.01); *G01N 15/0266* (2013.01)

(58) Field of Classification Search
USPC ........................................ 250/288, 281, 282
See application file for complete search history.

(56) References Cited

U.S. PATENT DOCUMENTS

| | | | |
|---|---|---|---|
| 6,960,761 B2 * | 11/2005 | Clemmer | G01N 27/622 250/287 |
| 7,189,977 B2 * | 3/2007 | Yamaguchi | H01J 49/165 250/288 |
| 7,820,966 B2 | 10/2010 | Bateman | |

(Continued)

FOREIGN PATENT DOCUMENTS

GB 2425650 A 11/2006

OTHER PUBLICATIONS

Sessions et al., "Moving-Wire Device for Carbon Isotopic Analysesof Nanogram Quantities of Nonvolatile Organic Carbon", Anal. Chem. 2005, 77, pp. 6519-6527.

(Continued)

*Primary Examiner* — Phillip A Johnston
(74) *Attorney, Agent, or Firm* — David A. Schell

(57) ABSTRACT

A sample introduction system for a spectrometer comprises a desolvation region that receives or generates sample ions from a solvent matrix and removes at least some of the solvent matrix from the sample ions. A separation chamber downstream of the desolvation region has a separation chamber inlet communicating with the desolvation region, for receiving the desolvated sample ions along with non-ionized solvent and solvent ion vapors. The separation chamber has electrodes for generating an electric field within the separation chamber, defining a first flow path for sample ions between the separation chamber inlet and a separation chamber outlet. Unwanted solvent ions and non-ionized solvent vapors are directed away from the separation (Continued)

chamber outlet. The sample introduction system has a reaction chamber with an inlet communicating with the separation chamber outlet, for receiving the sample ions from the separation chamber and for decomposing the received ions into smaller products.

27 Claims, 6 Drawing Sheets

(56) References Cited

U.S. PATENT DOCUMENTS

| | | | | |
|---|---|---|---|---|
| 7,960,711 | B1 * | 6/2011 | Sheehan | H01J 49/045 250/281 |
| 8,188,423 | B2 * | 5/2012 | Doroshenko | H01J 49/0045 250/281 |

OTHER PUBLICATIONS

Teffera et al., "Continuous-Flow Isotope Ratio Mass SpectrometryUsing the Chemical Reaction Interface with Either Gas or Liquid Chromatographic Introduction", Anal. Chem. 1996, 68, pp. 1888-1894.

* cited by examiner

IRMS SAMPLE INTRODUCTION SYSTEM AND METHOD

FIELD OF THE INVENTION

This invention relates to a sample introduction system for an isotope ratio mass spectrometer or isotope ratio optical spectrometer, and a method for coupling such an isotope ratio spectrometer (IRS) to a supply of sample entrained with a matrix/solvent.

BACKGROUND TO THE INVENTION

Isotope ratio mass spectrometry is a technique which accurately and precisely measures variations in the relative abundances of isotopes, i.e. isotopic ratios, of elements such as $^{13}C/^{12}C$, $^{18}O/^{16}O$, $^{15}N/^{14}N$ and $^{34}S/^{32}S$ in molecules.

Prior to analysis, a sample typically undergoes oxidation, pyrolysis or reduction at an elevated temperature to produce gases of molecules, for example, $CO_x$, $NO_x$, $H_2O$. The gases are then introduced into the IRS for isotopic analysis. In the isotope ratio spectrometer (IRS), the gases are ionised and the ratios of corresponding isotopes are measured for example by comparing outputs of different collectors. The ratios of the isotopes of interest are typically measured relative to an isotopic standard in order to eliminate any bias or systematic error in the measurements.

For isotopic analysis of specific compounds within a complex mixture, it is desirable to perform a separation prior to the isotopic analysis. Currently, this separation is performed by gas chromatography, which can be coupled to an IRMS using a combustion oven.

Liquid chromatography (LC) is an established technique in the field of biochemistry and pharmacology. However, coupling an IRS to a liquid chromatography system presents technical challenges because LC mobile phase is usually organic and therefore produces the same products as sample molecules of interest, thus interfering with the isotopic analysis. There have been various attempts at coupling liquid chromatography to IRMS, as identified below.

"Moving-wire device for Carbon Isotopic Analyses of Nanogram Quantities of Nonvolatile Organic Carbon" (A. L. Sessions, S. P. Sylva and J. M. Hayes, Anal. Chem., 2005, 77, 6519-6527) describes a method for analysing $^{13}C$ ratios of involatile organic samples dissolved in solution. The output solution of the separation system is dried onto a nickel wire to remove the mobile phase from the sample. The residual sample is then combusted and the evolved $CO_2$ is analysed by IRMS. However, both the precision and sensitivity of this method are limited by a high background level of $CO_2$ derived from carbon within the wire.

Another method of coupling a liquid chromatography system to an IRMS is presented in ""Continuous-Flow Isotope Ratio Mass Spectrometry Using the Chemical Reaction Interface with Either Gas or Liquid Chromatography Introduction" (Y. Teffera, J. Kusmierz, F. Abramson, Anal. Chem., 1996, 68, 1888-1894)". In this method, the solution exiting from the liquid chromatography system undergoes desolvation at semi-permeable membranes prior to chemical oxidation of the dry aerosol. The oxidised products are then analysed by IRMS. However, the method described does not remove the mobile phase to the required ultra-low levels of solvent, for example, to a solvent/sample ratio better than 1:100.

Wet chemical oxidation (LC-Isolink™) addresses the problem of both earlier methods and allows coupling to liquid chromatography. The solution output from the chromatography system is mixed with an oxidizing agent and supplied to an oxidation reactor. In the oxidation reactor the organic compounds are converted into $CO_2$, which is then analysed in the IRMS. However, there is no separation of the mobile phase from the sample and therefore, this method is not suitable for separation methods that require an organic mobile phase.

In the fields of pharmaceutical and life sciences, the typical sample includes organic molecules dissolved in an organic solvent. For such samples, separation of the molecules from the solvent is generally carried out with an organic mobile phase using techniques such as high performance liquid chromatography, capillary-zone electrophoresis and size-exclusion chromatography. As a result, the output of the separation apparatus also consists of an organic sample dissolved in an organic solvent.

The presence of this organic solvent would result in production of a large amount of $CO_2$ during combustion and hence an extremely high background $CO_2$ in the spectrum produced by IRMS.

In order for analysis by IRMS of an organic molecule dissolved in an organic solvent, a great reduction in the solvent/sample ratio from 100-1,000,000:1 to less than 1:100-1000 i.e. a reduction of 5-8 orders of magnitude or higher is required.

None of the existing techniques, as identified above, can reduce the organic solvent/organic sample ratio to the required ultra-low levels.

Therefore, a sample introduction system which can couple a supply of sample entrained with any solvent to an IRMS is required.

The present invention seeks to address this problem by providing a new approach to separation of sample molecules from more volatile molecules of the mobile phase.

SUMMARY OF THE INVENTION

According to a first aspect of this invention, a sample introduction system for an IRMS is provided.

As noted above, the challenge faced by current techniques for analysing a sample dissolved in a solvent, is how to reduce the organic solvent/organic sample ratio to the required ultra-low levels so that the solvent does not contribute significantly to the recorded spectrum, e.g. isotopic spectrum. In this way, an improved quantitation of isotopic ratios can be achieved.

The sample introduction system of the claimed invention requires ionization of the sample prior to decomposition, preferably in a spray ionization source. The ionised sample is then desolvated. The resulting desolvated ions are then preferably moved, optionally accelerated, in a separation chamber in first direction by an electric field whilst being moved in a second, different direction by, for example, a flow of gas, or an electric or magnetic field (static and/or varying). The result is that sample ions of a desired species having a particular mobility and/or mass to charge ratio (or range of mobilities and/or mass to charge ratios) are directed to an outlet of the separation chamber, for onward reaction/combustion/pyrolysis/reduction, whilst unwanted solvent ions and uncharged solvent molecules are forced either to move along a different path, or randomly/indiscriminately in multiple directions, so that, in either event, they do not pass out of the separation chamber for downstream analysis, and are instead swept away or lost.

The sample introduction system of the claimed invention differs from that employed in a typical IRS, in that it requires ionization of the sample prior to decomposition (by an ionisation source within the sample introduction system). The ionization takes place upstream of the separation chamber, which can then act to separate the sample from solvent ions and solvent vapour as described. The sample ions exiting the separation chamber into the reaction chamber are then decomposed therein to smaller products, typically molecular products (e.g. including one or more of $CO_x$, $NO_x$, $H_2O$ in the case of a combustion/oxidation chamber, x being typically 1 or 2) and the resultant decomposed products are analysed. In IRMS, this implies a further ionisation source to ionize the resultant decomposed products to permit subsequent analysis. In IR optical spectroscopy, isotope ratios of the resultant decomposed products may be determined from spectroscopic measurements in a cavity. For example, infra-red wavelengths corresponding to the greatest optical absorption of the products may be determined.

The pressure in the separation region is desirably lower than the pressure in the desolvation region, so that ions are drawn from the desolvation region and into the separation region as a jet. The geometry of the aperture or channel between the desolvation and separation regions may also be configured to improve transfer of ions into the separation region as known in the prior art. The sample introduction system preferably operates at around atmospheric pressure. For example, the desolvation region may be held at atmospheric pressure (100 kPa) whilst the separation chamber may be evacuated to a pressure preferably not more than half the pressure in the desolvation region, e.g. around 10-30 kPa (0.1-0.3 bar). Alternatively, the separation chamber may be held at around atmospheric pressure, with then the pressure in the desolvation chamber being raised to preferably at least twice that pressure, e.g. around 200-300 kPa (2-3 bar). Such a large difference in pressures is preferable because it creates a supersonic jet followed by shock waves, thus accelerating gas transfer between regions. This in turn reduces the dependency on sample and conditions (e.g. humidity) in the desolvation region.

Thus preferred embodiments of the present invention provide a way of removing large quantities of solvent at a relatively high pressure (preferably atmospheric pressure). Providing a way of removing solvent at relatively high pressure is desirable, since it provides increased efficiency and reduces sample losses. It also permits coupling to the reaction chamber, for decomposition of the sample ions. A pressure around atmospheric pressure in the separation chamber and higher in the desolvation region is thus most preferable.

The invention also extends to an IRMS or IROS having such a sample introduction system.

In addition to a sample introduction system, the present invention also extends to a method of introducing a sample into an Isotope Ratio Mass Spectrometer.

Further aspects of the present invention provide a sample introduction system for an IRMS, comprising a first ionization source arranged to receive a sample from a liquid sample preparation region and to ionize the received sample to produce sample ions in a solvent matrix, a desolvation region to remove at least a proportion of the solvent matrix from the sample ions, a separation chamber positioned downstream of the desolvation region for receiving the desolvated sample ions along with solvent vapours comprising non-ionised solvent and solvent ions, and separating out sample ions of interest for further analysis; a reaction chamber arranged to receive the separated sample ions of interest and to react the said sample ions of interest to produce products; and a second ionization source to ionize the products of the reaction chamber so as to produce product ions for analysis by an IRMS.

A method of sample introduction is also contemplated, which comprises receiving a sample from a liquid sample preparation region, ionizing, in a first ionization source, the received sample to produce sample ions in a solvent matrix, removing at least a proportion of the solvent matrix from the sample ions in a desolvation region, receiving, from the desolvation region, the desolvated sample ions along with solvent vapours comprising non-ionised solvent and solvent ions, and separating out sample ions of interest for further analysis in a separation chamber positioned downstream of the desolvation region; receiving the separated sample ions of interest in a reaction chamber, and reacting the said sample ions of interest to produce products; and ionizing, in a second ionization source, the products of the reaction chamber so as to produce product ions for analysis by an IRMS. That method may then also include mass analysing the product ions in an IRMS device.

BRIEF DESCRIPTION OF THE DRAWINGS

The invention may be put into practice in a number of ways and some specific embodiments will now be described by way of example only and with reference to the accompanying drawings in which.

DETAILED DESCRIPTION OF PREFERRED EMBODIMENTS

Figure 1:
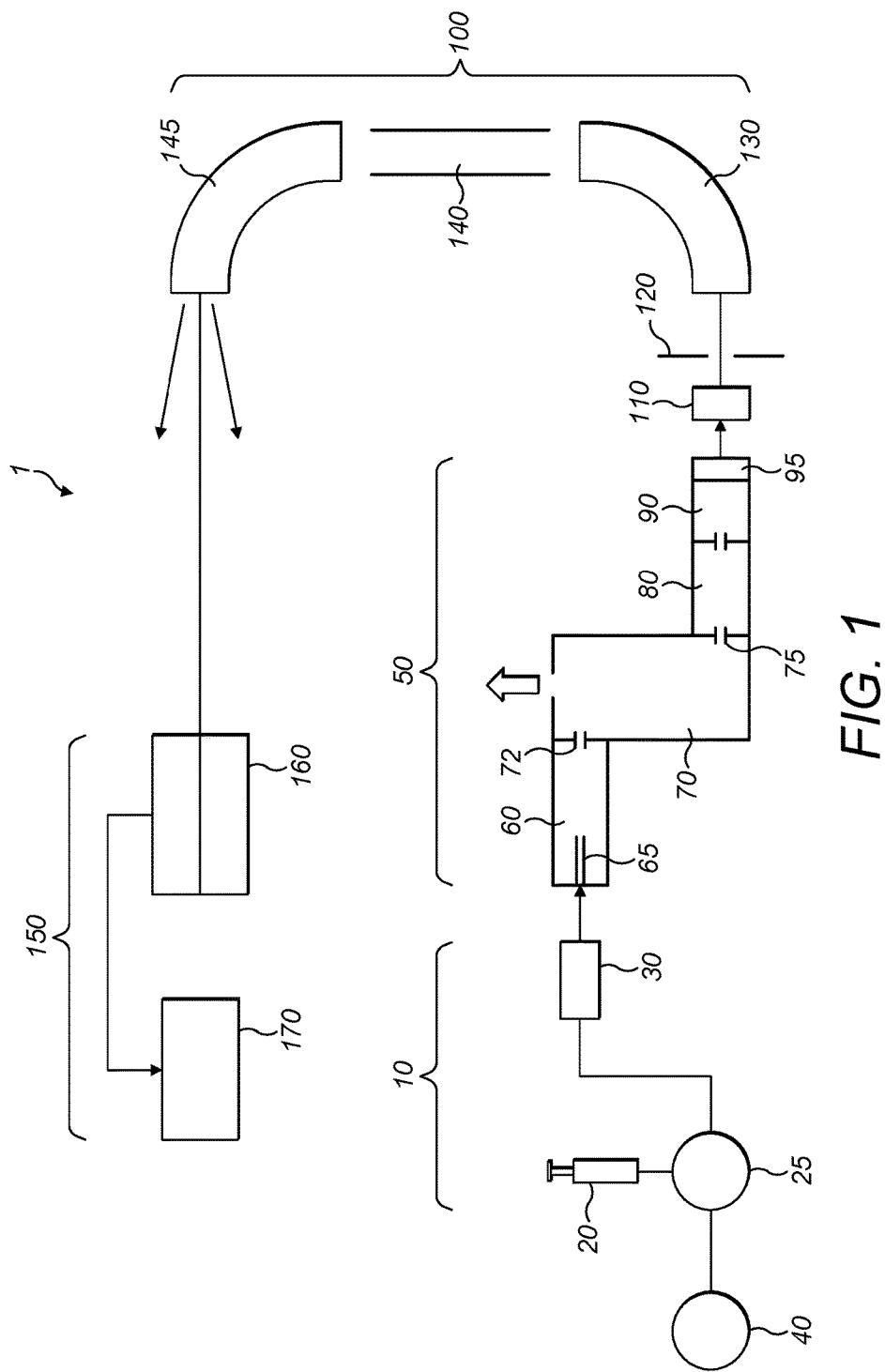
FIG. 1 shows a schematic view of a system comprising a liquid sample preparation region and a sample introduction system coupled to an isotope ratio mass spectrometer (IRMS)

FIG. 1 shows a schematic diagram of a system 1 comprising a liquid sample preparation region 10 and a sample introduction system 50 coupled to an isotope ratio mass spectrometer (IRMS) 100, having a detector 150.

The liquid sample preparation region 10 of the system 1 has an autosampler 20 for providing a sample to an injector 25 where the sample is entrained with a pumped liquid mobile phase. Embodiments of the present invention are particularly concerned with analysis of a pharmaceutical or life sciences sample, which typically contains large organic molecules dissolved in a liquid solvent which is a mixture of acidified water and organic solvent such as acetonitrile or methanol in varying ratios.

The sample entrained with the liquid mobile phase is provided to a liquid separator 30 by means of a pump 40. Any liquid separator 30 may be employed to separate a component or components of interest in the liquid sample, for example, capillary zone electrophoresis (CZE), high performance liquid chromatography (HPLC) or size exclusion chromatography (SEC) column. The liquid separator typically separates one or more components of the sample in the solvent matrix so that they elute from the liquid separator separated in time. The structure of the liquid separator as known in the art is not discussed in further detail here.

The output of the liquid separator (eluate) comprises the separated sample entrained in solvent. The output of the liquid separator 30 is fluidically coupled to an inlet of a sample introduction system 50.

The sample introduction 50 comprises a desolvation chamber 60 including a first ionization source 65. Various types of first ionization source 65 may be employed, such as a nanospray ionization source, thermospray ionization source, atmospheric pressure chemical ionization source, atmospheric pressure photo-ionization source, glow discharge or low-temperature plasma source, inlet ionization source etc. The first ionization source 65 receives the sample entrained with solvent, preferentially ionizes the sample, and evaporates the solvent from the sample in the desolvation chamber 60 so as to produce desolvated sample ions and solvent vapours. The solvent vapours comprise non-ionised solvent molecules and/or solvent ions. High efficiency of conversion of the sample into ions is important for good sensitivity of the method.

A separation chamber 70 downstream of the desolvation chamber 60 receives the desolvated sample ions and solvent vapours, via a separation chamber inlet 72. Within the separation chamber 70, the desolvated sample ions and solvent vapours experience an electric field (E) that moves or accelerates the desolvated ions from the entrance towards the exit of the chamber. Via a gas flow in a different direction to the electric field, via crossed electric and magnetic fields, via a combination of static and varying electric fields, or otherwise, sample ions of a selected mobility (or selected range of mobilities) are then directed towards a separation chamber outlet 75. This process will be described in further detail below, in connection with FIGS. 2 and 3.

The selected ions exiting the separation chamber outlet 75 enter a reaction or decomposition chamber. In FIG. 1, the reaction or decomposition chamber is a reaction chamber 80, positioned downstream of the separation chamber 70. In the reaction chamber 80, the ions of the selected species are decomposed at elevated temperatures, optionally in the presence of a catalyst, into a combination of light gases such as $CO_2$, $NO_x$, $H_2O$ and $H_2$.

A $CO_2$ separation unit 90 of the sample introduction system 50 is optionally positioned downstream of the reaction chamber 80 for selective removal of the $CO_2$ from the combusted sample in known manner. The $CO_2$ separation unit 90 comprises a membrane exchanger of planar geometry configured to separate $CO_2$ from the remaining gases. A flow of helium gas is provided in a direction normal to the plane of the membrane. In that case, the $CO_2$ gas is then carried in the flow of helium and may be dried using a dryer 95 (eg Nafion™). The $CO_2$ separation unit 90 is advantageous if the analysis to be performed by IRMS is specifically of $CO_2$.

The resulting gases (e.g. $CO_2$, $NO_x$, $H_2$, $H_2O$) then leave the sample introduction system 50 and enter the IRMS 100 either directly or via an open split. The IRMS may be any suitable known device, eg the Delta V_IRMS manufactured and sold by Thermo Fisher Scientific, Inc. Alternatively, an optical based isotope ratio spectrometer (e.g. Thermo Scientific Delta Ray™) may be employed, for analysis of $^{13}C/^{12}C$, $^2H/^1H$ or $^{18}O/^{16}O$ isotopic ratios etc.

Merely by way of example, therefore, FIG. 1 shows a first part of the IRMS 100 which comprises a second ionization source 110. The second ionization source 110 may, for example, be an inductively coupled plasma (ICP) ionization source or, where higher sensitivity is desirable, an electron impact (EI) ionization source, or the like. Ions generated by the second ionization source 110 are accelerated and then passed through an entrance slit 120 which controls the ions entering the IRMS 100, and determines the IRMS 100 resolution.

The accelerated ions then enter an optional electric sector 130, a set of ion optics 140, and a magnetic sector 145. Ions are thus separated in accordance with their mass to charge ratio and arrive at a detector arrangement 150 positioned at the focal plane of the ion beam. The detector arrangement 150 contains a detector 160 which may, for example, be a multiple collector arrangement under the control of a controller 170. The controller may also comprise a data acquisition system. A single detector may alternatively be used e.g. with scanning of the ion mass-to-charge ratio by the magnetic sector.

The details of the ion separation in the liquid phase and detection downstream of the sample introduction system 50 do not form a part of the present invention and so will not be described in further detail. It will moreover be understood that various types of IRMS spectrometer may be employed, such as continuous flow and duel-inlet IRMS.

Figure 2:
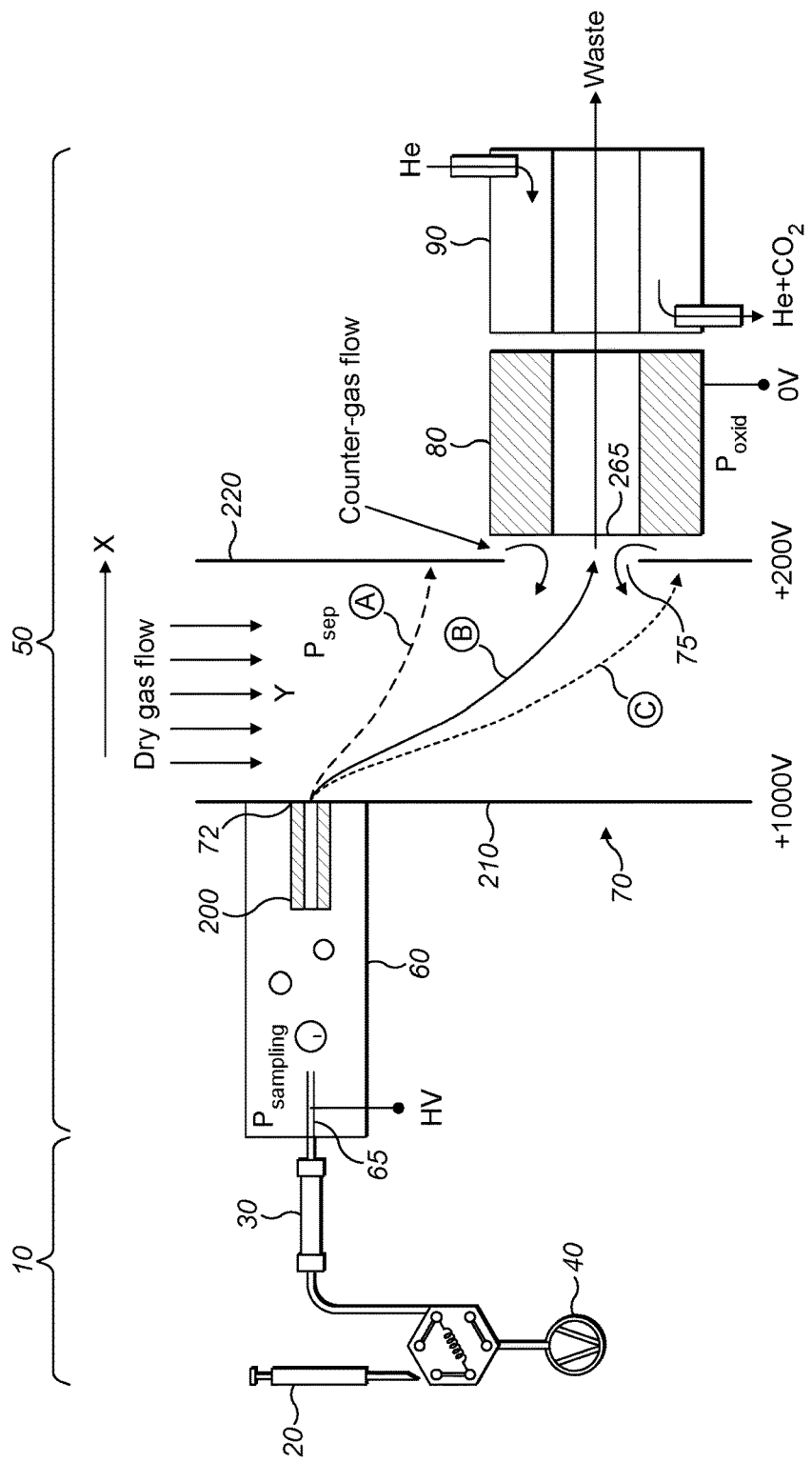
FIG. 2 shows, in further detail, the liquid sample preparation region and sample introduction system of FIG. 1, the sample introduction system being in accordance with a first exemplary embodiment of the present invention.

Having described, in general terms, the stages of ionization, separation, decomposition and detection of sample ions of interest, the manner by which pyrolized or combusted or reduced sample ions can be introduced to the IRMS, whilst solvent molecules are removed, will now be described with reference to FIGS. 2 and 3. FIG. 2 shows a more detailed schematic diagram of a sample introduction system 50, into which an eluate is introduced from a liquid sample preparation region 10.

As explained above in connection with FIG. 1, the sample injector 20 injects a sample entrained with liquid mobile phase into the liquid separator 30 by a pump 40. The eluate output from the liquid separator 30 then enters desolvation chamber 60. It is to be noted that, in any liquid separation, the $^{13}C$ or $^2H$ isotope-containing molecules might elute slightly differently from the base-isotope molecule, leading to noticeable fractionation. It is desirable to correct for any such fractionation.

Upon entering the desolvation chamber 60, the eluent from the liquid sample preparation region 10 is converted into charged droplets and then, after desolvation of the droplets, ions by the first ionization source 65 which is, as noted above, preferably a spray ionization source. The resultant ions travel across the desolvation chamber towards a heated channel 200 which guides sample ions towards an outlet of the desolvation chamber 60.

It is preferable that the arrangement of FIG. 2 employs a planar geometry, that is, the sectional view shown in FIG. 2 extends orthogonally to the plane of the drawing. The heated channel 200 may be, for example, between 0.8 and 1 mm high and 5-10 mm wide and between 20 and 100 mm in length, which is heated up to 500-700° C. The heated channel dimensions define the opening of the separation chamber inlet 72. Such an opening allows transmission of between 10 and 100 nA of ion current into the separation chamber 70.

In addition to the heated channel 200, a flow of heated gas may additionally or alternatively be supplied to the desolvation chamber 60. Both the heated channel 200 and the heated gas flow may significantly improve the degree of desolvation of the ionized eluent entering the desolvation chamber 60.

The pressure in the desolvation chamber 60, $P_{sampling}$, may be greater than, the same as or less than atmospheric pressure $P_0$. The relative pressures in the various parts of the sample introduction system 50 may assist in the removal of unwanted solvent prior to injection into the IRMS 100.

In order to achieve efficient and rapid transfer, it is preferable that the pressure in the separation chamber 70 is lower than the pressure in the desolvation chamber 60. In particular, it is preferable to form a jet leaving the aperture 72 between the desolvation chamber 60 and separation chamber 70, with $P_{sampling} > 2*P_{sep}$, where $P_{sep}$ is the pressure within the separation chamber 70. For example, $P_{sampling}$ may be between 200-300 kPa (2 to 3 bar), whilst $P_{sep}$ equals $P_0$ (that is, the separation chamber is held at atmospheric pressure). Alternatively, $P_{sampling}$ equals $P_0$—i.e. the desolvation chamber 60 is held at atmospheric pressure, whilst in that case $P_{sep}$ equals 10-30 kPa (0.1-0.3 bar). One or more pumps (not shown in FIG. 2) may be provided in order to adjust the pressure within the separation chamber 70 and/or desolvation chamber 60, above or below atmospheric pressure.

The separation chamber 70 of FIG. 2 separates ions of different species, and removes unwanted neutral solvent molecules, using a technique known as differential mobility analysis (DMA). The general principles of the technique are described in, for example, U.S. Pat. No. 5,869,831.

The separation chamber 70 of FIG. 2 comprises first and second generally planar electrodes 210, 220 which are located in opposition to one another across a separation gap in the longitudinal direction of the sample introduction system 50. The first and second electrodes 210, 220 are separated by a gap in the range of 10-50 mm with gas blown in by a fan or sucked away by a pump. The separation chamber inlet 72 is formed in or through the electrode 210 whilst the separation chamber outlet 75 is formed in or through the electrode 220. Each aperture is, preferably, slit shaped (e.g. of the dimensions noted above for the slit shaped heated channel 200).

The voltages applied to each of the electrodes 210, 220 are selected on the basis of the sample ions of interest in the sample. As shown in FIG. 2, in the specific example provided, the first electrode 210 has a voltage of 1000 volts applied to it whilst the second electrode 220 has a voltage of 200 volts applied to it. For pressures in the range 10-1000 Pa (0.1-10 mbar), it is preferable not to exceed 300V between the electrodes 210 and 220, in order to avoid gas discharge. Ions of different species A, B and C have different mass to charge ratios and are accordingly accelerated to different drift velocities within the separation chamber 70.

The desolvated sample ions and solvent vapours enter the separation chamber 70 via inlet 72 as a jet, in a direction X as shown in FIG. 2. A dry, ion free inorganic gas, preferably of high or ultra-high purity, is supplied in a direction Y transverse to the direction X (in other words, transverse to the longitudinal axis of the sample introduction system 50). In FIG. 2, the dry gas is introduced in a direction Y that is perpendicular to the direction X. However it will of course be understood that the dry gas may be introduced at any suitable angle relative to the direction X, provided only that the dry gas flow direction intersects the direction of flow of ions as they enter the separation chamber 70 and are accelerated by the DC electric field.

The separation chamber inlet 72 is offset from the separation chamber outlet 75 in the Y direction. The combination of the DC electric field accelerating ions in the direction X and the dry gas flow imparting a component of movement to the ions in the direction Y, is that ions describe flow paths having both an X and a Y component as they travel across the separation chamber 70. Ions of different species have different masses and collisional cross sections, so that the interaction between molecules of the dry gas and ions within the separation chamber 70 will differ between ion species in the separation chamber 70. In other words, ions of a first species A having a first electrical mobility (first mass and collisional cross section), will be deflected along a first path. Ions of second and third species B, C, having respective second and third electrical mobilities (mass/collision cross sections), however, will be deflected respectively along second and third paths, each different to one another and to the first path. In the example shown in FIG. 2, the particular combination of applied voltages and gas flow chosen, results in the deflection of ions of species B (and only these) into the separation chamber outlet 75. Generally speaking the direction of travel of wanted sample ions entering the reaction chamber 80 is in the X direction, i.e. parallel with the direction of flow of ions in the jet entering the separation chamber 70, but shifted in the Y direction.

In this manner, dust and unwanted neutral and charged solvent molecules, which typically form as large clusters with high mass to charge ratios and high collisional cross sections, can be separated from wanted sample ions via the separation chamber 70, because the solvent clusters have too high a collision cross section to follow the trajectories of the sample ions. Moreover, neutral solvent molecules entering the separation chamber 70 will not be accelerated by the electric field towards the electrode 220, and so will also be swept away by the flow of dry gas.

If the end goal of the sample analysis is to study C or O isotopic ratios, then the dry gas may be, for example, argon, nitrogen or the like. For analysis of N isotopes, argon or oxygen might instead be employed. The sample introduction system 50 is, of course, not limited only to such elemental isotopes, and could equally be employed to study isotopic ratios of $CO_2$, $H_2$/HD for pharmaceutical and life sciences, and so forth.

As a result of the markedly different electrical mobilities of the sample and solvent ions, typically a very low resolving power of separation (perhaps 2-3) is sufficient to separate the sample and solvent ions. Appropriate resolving power is defined by selecting appropriate geometrical and electrical parameters of the separator. Such a very low resolving power of separation results in a uniform transmission of sample molecules of broad mass range and negligible isotopic discrimination. Calibration compounds can be employed to generate correction coefficients to take into account efficiency of ionization. The strong electric field is created by a voltage drop between the electrodes 210 and 220 and the optional heated channel 200 at the exit of the desolvation region 60 may permit complete desolvation of the sample ions.

In the embodiment of FIG. 2, the reaction chamber 80 is coupled to the separation chamber outlet 75 via a reactor inlet 265. At this interface, it is desirable to provide a counter flow of dry inorganic gas so that any solvent molecules that still remain entrained with the wanted sample ions upon arrival at the separation chamber outlet 75 are prevented from entering the reaction chamber 80. To achieve this, it is desirable that the pressure $P_r$ within the reaction chamber 80 (which could alternatively be a pyrolysis or reduction chamber) is higher than the pressure in the separation chamber 70 (i.e. $P_r > P_{sep}$). Then, the DC electric field in the separation chamber 70 applies a force in the positive X direction to wanted sample ions to drive them into the reaction chamber 80, whilst the counterflow of gas is drawn into the separation chamber 70 from the direction of the reaction chamber 80 by the pressure difference in the negative X direction.

The reaction chamber 80 is preferably a non-porous aluminium tube that contains three separate twisted wires made of copper, nickel and platinum and is typically maintained at 1030 degrees Celsius. This type of reaction chamber is described in http://stableisotopefacility.ucdavis.edu/ASITA/Eby-presentation1.pdf.

Figure 3:
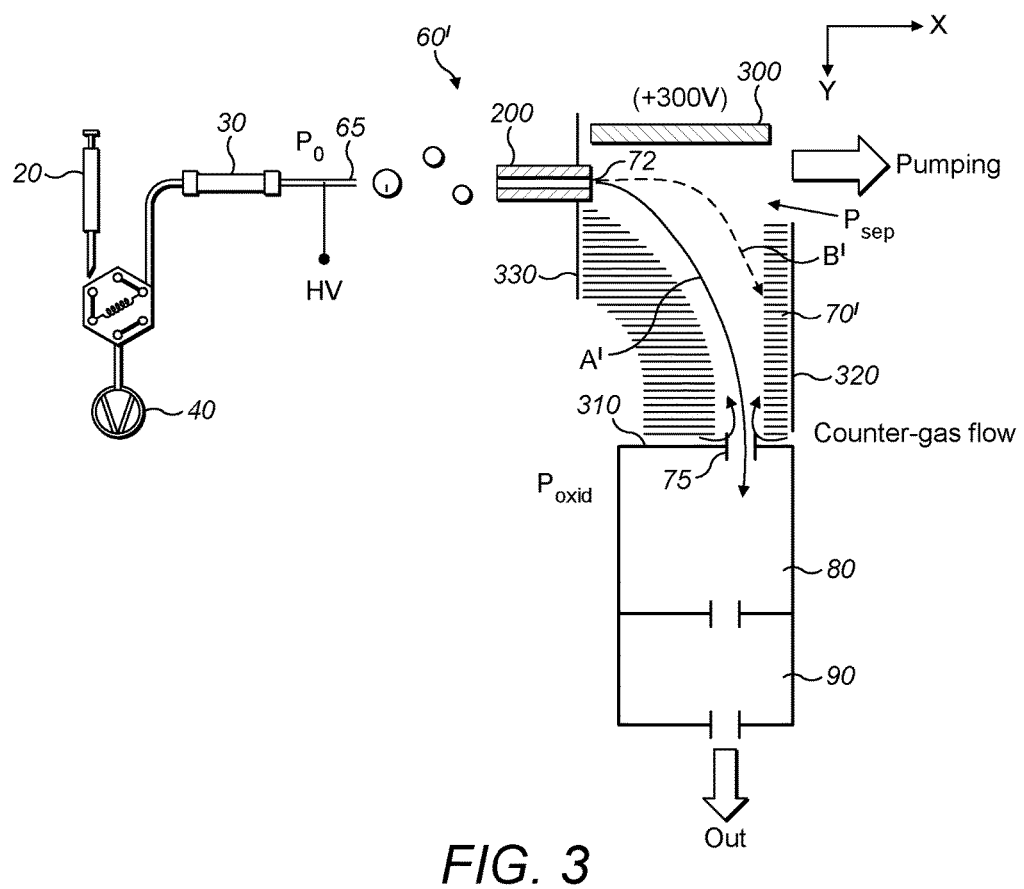
FIG. 3 shows, also in further detail, the liquid sample preparation region and sample introduction system of FIG. 1, the sample introduction system being in accordance with a second exemplary embodiment of the present invention.

FIG. 3 shows an alternative arrangement of a sample introduction system 60', into which an eluate is introduced from the liquid sample preparation region 10. Those components which are common to FIGS. 2 and 3 are labelled with like reference numerals. Where the function of the common parts is the same as between FIGS. 2 and 3, this will be indicated below to avoid repetition.

In FIG. 3, an eluate is generated by a liquid separator 30 fed from a sample injector 20 by a pump 40. The eluate then enters a first ionization source 65 forming an upstream part of a desolvation region 60'. The first ionization source 65 may be of any of the same types as described above in respect of FIG. 2. The desolvation region 60' is, in the exemplary embodiment of FIG. 3, not sealed against outer atmosphere. The pressure $P_{sampling}$ in the desolvation region 60' is thus atmospheric ($P_{sampling}=P_0$).

Ions generated by the first ionization source 65 traverse a gap and arrive at a heated channel 200, whose function and configuration may be as previously described. From there, desolvated ions and remaining solvent vapours enter a separation chamber 70'. The separation chamber has an inlet 72 through which the heated channel 200 extends, so that the heated channel directs the desolvated ions and solvent vapours into the separation chamber 70' in a direction generally parallel with the X direction shown in FIG. 3.

Extending in the +/−X direction is a first DC electrode 300. An aperture plate 310 is separated from the first DC electrode in the Y direction, and a separation chamber outlet 75 is formed in that aperture plate 310. A power supply (not shown) applies a potential difference of substantially constant voltage between the first DC electrode 300 and the aperture plate 310; for example the aperture plate 310 may be grounded whilst a potential of 300V is applied to the first DC electrode 300. Such a potential difference results in a DC electric field being generated in the separation chamber 70'. The separation chamber inlet 72 is positioned between the first DC electrode 300 and the aperture plate 310, so that ions entering the separation chamber 70' as a jet in the direction X experience a force in the Y direction. The combination of the velocity of the ions in the jet that enters the separation chamber 70' (in the direction X), and the electric field that imparts a force in the direction Y, causes ions to commence a curved trajectory.

Extending in the +/−X direction to either side of the separation chamber 70' are first and second combined AC/DC electrode stacks 320,330. The power supply is configured to apply an RF voltage to the first and second AC/DC electrode stacks 320, 330,—for example by applying opposite RF phases to successive ring or plate electrodes in the stacks. Both stacks could be thus united into a single stack. The RF electric field produced by applying an RF potential to the stacks acts to prevent ions from landing on the electrodes and guide them through the separation chamber 70'.

The power supply is also configure to apply a DC voltage to the stacks, for example by using a (resistive) potential divider connected to each of the rings or plate electrodes in the stacks so as to permit a DC potential gradient to be applied. As the ions enter into the separation chamber 70', there is no gas pressure to propel them towards the aperture 75, so the DC gradient applied to the first and second AC/DC electrodes 320,330 results in ions being pulled away from the separation chamber inlet 72.

The alternating phases of RF applied to the first and second AC/DC electrodes 320, 330 are of a frequency and amplitude that results in wanted sample ions being guided along a path marked A', away from the electrodes and into the separation chamber outlet 75. Meanwhile unwanted solvent and other ions are lost to the side walls of the separation chamber, because neutral solvent molecules experience no electric field and hence no accelerating or guiding force, and because any charged solvent ions (in particular) tend to aggregate as heavier clusters and are thus incapable of following the RF field. As may be seen in FIG. 3, the central axis and direction of travel of ions entering the separation chamber 70' as a jet through the inlet 72, is generally at right angles to the central axis and direction of travel of ions as they exit the separation chamber 70' through the outlet 75. This arrangement means that there is no direct line of sight between the inlet 72 and outlet 75, preventing any uncharged solvent molecules, particulates and the like from passing from the inlet 72 to the outlet 75 as a result solely of an initial kinetic energy upon entering the separation chamber 70'.

It is preferable that the RF frequency applied to the first and second AC/DC electrodes 320, 330 is in excess of 10% of the collision frequency of the residual gas in the chamber, i.e., mainly, the residual gas from the desolvation region 60', such as Nitrogen for example. It is also preferable that the RF amplitude be less than half of the breakdown voltage of the residual gas at the chosen pressure of the separation chamber 70'.

As will be understood by the skilled person, the electrode arrangement in the separation chamber 70' takes the form of an RF ion guide/mass filter, and it is thus desirable that the separation chamber be evacuated to a relatively low pressure, to reduce collisional losses.

The separation chamber 70' is preferably evacuated to a pressure of no more than around 5,000 Pa, but preferably to a pressure not lower than around 10 Pa using a pump (not shown in FIG. 3).

As with the arrangement of FIG. 2, it is desirable in the arrangement of FIG. 3 that there is a pressure drop between the desolvation region 60' and the separation region 70', so as to assist in the creation of a jet of ions and entrained solvent molecules as they enter the separation region 70'. Although this is achieved in the specific configuration shown in FIG. 3 by evacuating the separation chamber 70', so that the desolvation region 60' may remain at atmospheric pressure and hence not require enclosure/sealing, it will of course be understood that the desolvation region 60' could be enclosed so as to allow different pressures (particularly, pressures above or below atmospheric pressure) to be set in the desolvation region 60'. As explained above, in order to employ RF ion guide and/or mass filtering techniques in the separation chamber 70', a relatively low pressure is desirable in that chamber (typically <50 mbar (5 kPa), preferably <0.2 mbar (20 Pa)). A quadrupole mass filter could be used in the separation chamber under such pressure conditions as a means to separate sample and solvent ions. Whilst, as described, this can be achieved by retaining the desolvation region 60' at atmospheric pressure and then pumping the separation chamber 70', by enclosing the desolvation region 60', staged evacuation can be employed, wherein the liquid sample preparation region 10 is held at atmospheric pressure, whilst the desolvation region 60' is roughly pumped to a fraction of an atmosphere and the separation chamber 70' is then evacuated to a few thousand Pa, down to a few Pa or even lower. Enclosing the desolvation region 60' also facilitates the use of a heated flow gas there, to assist in desolvation of the ionized eluent. The choice of whether the desolvation or separation chamber is sustained at atmospheric pressure, is determined mainly by the properties of the reaction chamber. For example, in many cases it is beneficial to keep it at a pressure close to atmospheric pressure, in order to ensure efficiency of reaction. Atmospheric pressure also facilitates the requirement to move gases with appropriate velocities, and promotes ease of cleaning.

Sample ions exiting the separation chamber 70' enter a reaction or decomposition chamber such as a reaction chamber 80. The reaction chamber may, as with the arrangement of FIG. 2, be held at a pressure $P_{oxid}$ higher than the pressure $P_{separation}$ in the separation chamber 70'. This again permits the use of a counter gas flow from the reaction chamber 80 into the separation chamber 70' via the separation chamber outlet 75, for the reasons previously explained. Ions could be transported against such flow using DC gradients for transport and RF fields for confinement.

Sample ions are then combusted in the reaction chamber 80. Optional $CO_2$ separation may take place in a $CO_2$ separation unit 90, the sample ion flow may further optionally dried, and then isotopic ratio analysis may be carried out by the IRMS 100 (FIG. 1).

The detection limit of the sample introduction system 50 described in FIGS. 1, 2 and 3 above is mainly defined by the number of ions necessary to acquire a sufficient statistical accuracy of an isotopic ratio in the IRMS. As an example, for a typical current of 1 nA of a molecule with 20 carbon atoms, about $10^{11}$ molecules of $CO_2$ per second will be produced. At 100% ionisation efficiency, which is typical for high proton affinity molecules, several picograms/second would be sufficient to deliver such a current, with higher loads leading to saturation of the current.

The relatively low ionisation efficiency of the electron-impact ion source in a standard IRMS (around 1 ion per 900 molecules) results in a reduction by around 3 orders of magnitude, ie to around $10^8$ ions of $CO_2$ per second. As a result, a statistically-limited accuracy of the isotope ratio for $^{13}C/^{12}C$ (with $^{13}C$ at 1.1% of $^{12}C$) is around 0.1% rms over one second of acquisition. This is typically more than sufficient for routine measurements in life science and (bio)-pharma applications, for labelling experiments, etc. As the typical LC peak width is on the scale of several seconds, online isotope ratio measurement becomes feasible notwithstanding possible peak tailing caused by combustion and $CO_2$ separation.

To compensate for the low ionisation efficiency in IRMS, high currents of sample ions are desired, up to microAmperes. This current (along with a high efficiency of ionisation) could be provided by an array of spray probes operating in parallel, each preferably spraying less than 1 microliter/minute of eluent. A flat geometry of a heated channel 200 and separation chamber 70 would support such parallel operation, with slit shaped separation chamber inlets 72 extending into the range of tens of mm. Such larger inlets are capable of removing limitations caused by space charge.

Although some specific embodiments have been described, it will be understood that these are merely for the purposes of exemplary illustration of the invention and are not to be considered limiting thereof. Various modifications and additions may be contemplated. For example, although the embodiments of FIGS. 1, 2 and 3 all describe the use of liquid samples with LC separation, ions might also be produced from a solid sample by techniques such as Matrix Assisted Laser Desorption Ionization (MALDI), direct electrospray ionization (DESI), direct analysis in real time (DART), etc.

Moreover, it is to be understood that the specific separation techniques described in connection with FIGS. 2 and 3 (using cross gas flow and combined DC/DC/AC fields respectively) merely serve to exemplify the general principles underlying the present invention. Generally speaking, it is necessary only that the separation chamber 70 be configured to transport wanted sample ions along an ion path across the chamber from the inlet 72 to the outlet 75 by the application of an electric field (AC and/or DC), whilst unwanted solvent ions and molecules are forced to move along either another path that prevents them from passing through the outlet 75 and into the reaction chamber 80, or causes the unwanted solvent ions/molecules to move indiscriminately in multiple directions. For example, separation of sample and solvent ions may be achieved through the use of a Field Asymmetric Ion Mobility (FAIMS) device. Such a technique is shown in U.S. Pat. No. 6,690,004, which proposes a planar FAIMS arrangement, and in WO-A-00/08454 which shows a coaxial arrangement. In each case, sample and solvent ions are separated not on their mobility (which is linked to collision cross section and thus directly to m/z), but on differential mobility, which is more dependent upon the chemical structures of the respective ions.

According to the above, the separation chamber may therefore, as a means to separate sample ions from interfering solvent ions and solvent molecules, comprise at least one of:

(i) an ion mobility separator (IMS), especially with transverse gas flow, and/or preferably with off-set inlet and outlet, (ii) an RF ion guide, optionally with DC axial field, having its longitudinal axis different (preferably perpendicular) to the axis along which ions enter the separation chamber, or having a curved axis (curved away from the axis along which ions enter the separation chamber).

(iii) a mass filter, for example a quadrupole mass filter, optionally with a curved axis, or axis different to the axis along which ions enter the separation chamber (iv) an array of miniature (micrometer- or even nanometer-size) mass filters arranged to divert ions away from neutral flow (v) a Field Asymmetric Ion Mobility (FAIMS) device.

The arrangements of FIGS. 1 and 2 show, for the purposes of illustration, a reaction chamber 80 connected to the separation chamber 70. However it is to be understood that this is merely an example of a suitable decomposition or reaction chamber, and other techniques for generating products may be used.

Figure 4A:
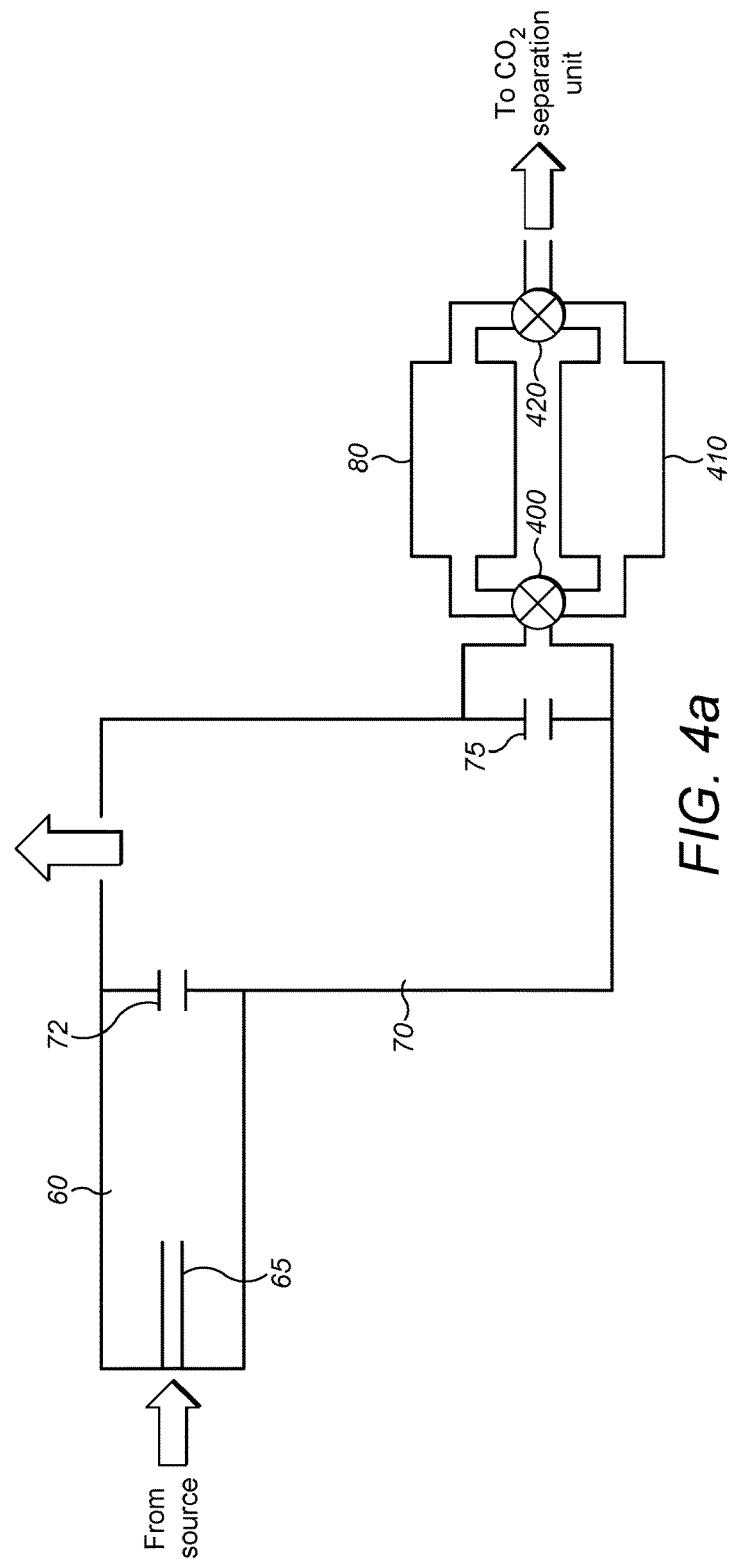
FIGS. 4a and 4b show schematic arrangements of alternate sample reaction arrangements suitable for the sample introduction systems of FIGS. 1-3.
Figure 4B:
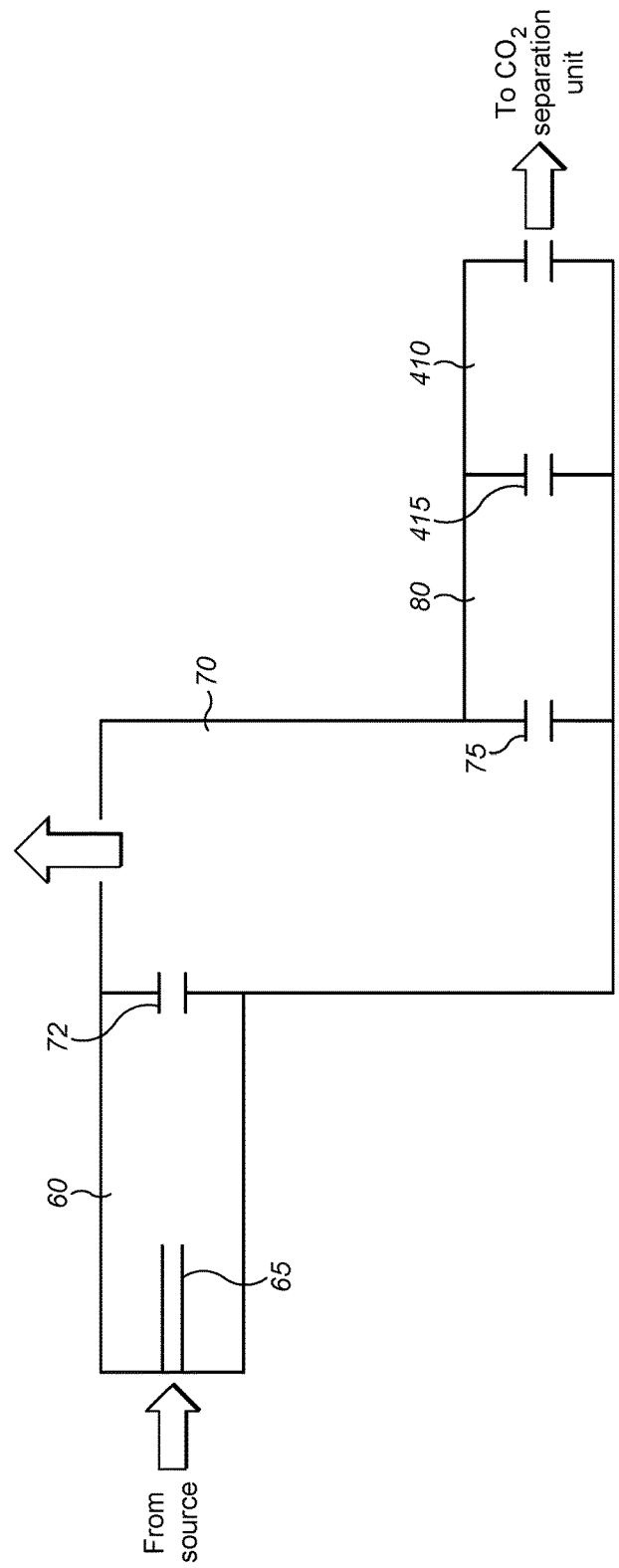

FIGS. 4a and 4b show, respectively, schematic drawings of a part of the sample introduction system of FIGS. 1, 2 and 3, with first and second alternative arrangements for reacting/combusting the ions arriving through the separation chamber outlet 75. In order to avoid repetition, those features common to FIGS. 1-3 and FIGS. 4a and 4b, will not be described in detail here. Moreover, the separation chamber in FIGS. 4a and 4b has been deliberately shown in highly schematic form, since the concepts to be described below in respect of FIGS. 4a and 4b are equally applicable to either of the different specific separation chamber arrangements of FIGS. 2 and 3.

Turning first to FIG. 4a, ions pass through the desolvation region 60 and into the separation chamber 70 through the inlet 72. Here, ions are separated as previously described and ions of interest are guided/directed out of the separation chamber 70 via the outlet 75.

Upon exiting the separation chamber, ions pass along a conduit to a first valve 400. The valve is switchable between a first position, in which ions arriving at it are directed along a first path into a reaction chamber 80, and a second position in which ions arriving at the first valve 400 are directed along a second path and into a pyrolysis or reduction chamber 410. The valve may be either manually operated or under software control so that, for example, a first set of ions may be combusted during a first period and then a second subsequent set of ions may be pyrolized during a second subsequent period (or vice versa).

Alternatively, the valve 400 may be configured to split the ion stream arriving at it so as to send part of the stream along the first path through the reaction chamber 80, whilst another part of the stream travels along the second path through the pyrolysis chamber 410, simultaneously.

Following combustion or pyrolysis in the respective combustion or pyrolysis chamber 80, 410 respectively, the resultant (usually neutral) molecules or elements pass along further conduits and through a second valve 420 (either in series, if the first valve 400 is set to send ions either to one or other of the combustion chamber 80 or pyrolysis chamber 410, or in parallel if the ions are split so as to pass through both the combustion chamber 80 or pyrolysis chamber 410 simultaneously), From the second valve 420, the products pass to the (optional) carbon dioxide separation unit 90 (FIGS. 1-3) for onward reionization and mass spectrometric analysis.

FIG. 4b shows an alternative configuration of a combustion chamber 80 in series with the pyrolysis chamber 410, rather than parallel as in FIG. 4a. In particular, in FIG. 4b, ions from the desolvation chamber 60 pass through the separation chamber 70 and are separated there. Ions of interest pass through the outlet 75 and enter the combustion chamber 80. If it is desired to combust the ions, then this chamber is suitably heated. Ions then exit the combustion chamber through an exit 415 into the pyrolysis chamber 410. Where the ions have been combusted, the pyrolysis chamber 410 is not heated and simply acts as a conduit for the combusted ions, which pass through the pyrolysis chamber 410, and out into the optional $CO_2$ separation unit 90 (FIGS. 1-3) for subsequent analysis.

Where on the other hand it is desired to pyrolize the ions, the combustion chamber is instead not heated and simply guides incident ions from the separation chamber 70 through the combustion chamber 80 and into the pyrolysis chamber 410. The latter is heated so as to pyrolize the ions before the resulting products are passed to the optional $CO_2$ separation unit 90 (FIGS. 1-3) for subsequent analysis, instead.

As a further optional configuration, instead of simply directing the output of the sample introduction system 50 into the combustion chamber 80 and/or pyrolysis chamber 410 and from there to an IRMS 100, for isotopic ratio measurements, a part of the resulting ions (such as a minor part, for example, around 10% or less) might be diverted to a conventional organic mass spectrometer, for carrying out analysis of sample ions (MS) and/or their fragments (MS/MS; MS"). Suitable instruments for such organic mass analysis are the triple quadrupole, or high resolution, accurate mass (HR-AM) devices such as the Exactive™ or Q Exactive™ instruments, manufactured by Thermo Fisher Scientific, Inc, which comprise an electrostatic orbital trap mass analyzer. Such an arrangement permits the analysis of isotopic ratios as well as molecular ions and their fragments—and hence the molecular structure of the sample ions—in one workflow—potentially even in one dataset.

Also, more than one mass spectrometer could be used. For example, while most of ions (>90%) are transferred to combustion chamber and then to IRMS, remaining may be sampled into a conventional mass spectrometer, e.g. triple quadrupole, HR/AM instrument like Q Exactive (orbital trap), multi-reflection TOF, etc. In this way, both isotopic ratio and molecular/structural information is obtained simultaneously and possibly, in one data set.

Figure 5:
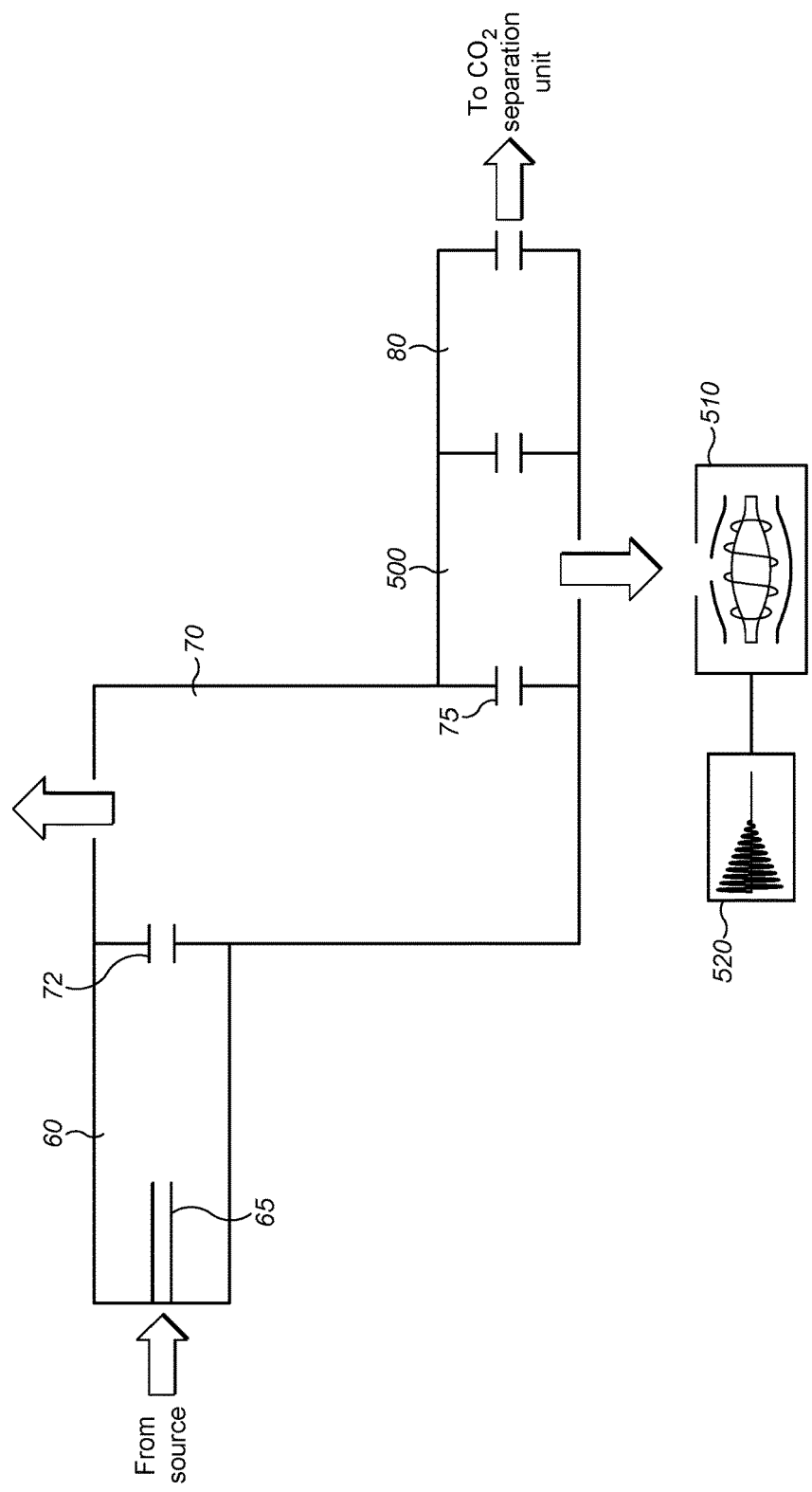
FIG. 5 shows a schematic arrangement of a part of the liquid sample preparation region and sample introduction system of FIGS. 1, 2 and 3, coupled with an orbital trapping mass spectrometer.

One exemplary configuration to illustrate these concepts is shown in FIG. 5. Again this is a highly schematic diagram which (deliberately) does not specify the particular arrangement of the separation chamber 70/70'. FIG. 5 shows a part of the system of FIG. 1. Ions from the desolvation chamber 60 pass through the separation chamber where they are separated as previously described. Ions of interest arrive at the outlet 75 and then enter an ion storage device 500 where they may be cooled and stored. A first set of ions may be ejected in a first direction—for example, axially as shown, where they enter a combustion chamber 80. From here, the ions are combusted and products enter the optional $CO_2$ separation unit 90 (FIGS. 1-3) for subsequent analysis by the IRMS 100 (FIG. 1).

A second set of ions held in the ion storage device 500 may instead be ejected in a second direction—for example orthogonally—towards an organic mass analyser 510 which in the example shown in FIG. 5 is an electrostatic orbital trap mass analyser. A transient signal 520 is thereby obtained, from which a mass spectrum can be generated.

The ion storage device 500 may be any suitable device, such as a linear or 3D trap. To permit orthogonal ejection of ions stored in the ion storage device 500 towards the electrostatic orbital trap mass analyser 510 shown in FIG. 5, the ion storage device 500 might for example be a curved linear trap.

By storing the ions passing through the outlet 75 in the separation device 70 in an ion storage device 500, those ions selected to be analysed by the organic mass analyser 510 may be ejected directly thereto without further treatment. Meanwhile, ions to be combusted pass through the reaction chamber 80. The resultant products subsequently then require further ionization using the second ionization source 110 (FIG. 1). A technique has been described in which ions enter the ion storage device 500 and are then directed in different ways, depending upon what is to be done with them (combustion or otherwise). However, the ions introduced into the ion storage device 500 need not be of a single species (or single, fixed range of species) during all such analyses. The ions can instead be selected in accordance with their subsequent treatment. For example, during a first period, ions of a first species (or range of species) may be selected, by appropriate configuration of the electric fields in the separation chamber 70/70', may enter the ion storage device 500, and then those ions may be ejected to the reaction chamber 80 for subsequent combustion and analysis by the IRMS 100. In a second time period, the electric field in the separation chamber 70/70' may instead be configured to select ions of a second species (or second range of species), different to the first, which are then trapped in the ion storage device 500 and instead ejected to the organic mass analyser 510 for analysis there.

Of course, the configurations of FIGS. 4a, 4b and 5 are entirely compatible: in other words, instead of simply ejecting ions from the ion storage device 500 into a reaction chamber 80, they could instead be ejected to a serially configured combustion and pyrolysis chambers (FIG. 4b) or a parallel arrangement with valves (FIG. 4a).

One potential practical implementation of the liquid sample preparation region and sample introduction system described above may be achieved by modification of the Q Exactive hybrid quadrupole-Orbitrap mass spectrometer manufactured by Thermo Fisher Scientific, Inc. The arrangement of components is shown schematically in, for example http://planetorbitrap.com/q-exactive. In the Q-Exactive mass spectrometer, ions are typically generated by an atmospheric pressure electrospray (ESI) source, and then injected into a first stage of the apparatus. This first stage may be configured to act as the desolvation chamber 60 of earlier Figures. It has a heated channel which may be used as the heated channel 200 of FIG. 2, for example.

Downstream of the first stage acting as a desolvation chamber 60, is a bent multipole ion guide which may remove neutral ions whilst transmitting charged analyte particles of interest. After that is a quadrupole mass filter which can be configured as a separation chamber 70. Finally, the Q-Exactive device comprises an Orbitrap mass spectrometer. This may be employed if the arrangement of FIG. 5 above is desired. A suitable reaction chamber may then be added to the back end of the Q-Exactive device.

In order to achieve effective oxidation, it is desirable that relatively high pressures are employed (in particular, many Pa). It is therefore preferable to use just the first one or two pumping stages of the Q-Exactive interface. It may also be necessary subsequently to increase the pressure again.

The invention claimed is:

1. A sample introduction system for a spectrometer, comprising:
   a desolvation region, arranged to receive or generate sample ions from a solvent matrix, and to remove at least a proportion of the solvent matrix from the sample ions;
   a separation chamber positioned downstream of the desolvation region and having a separation chamber inlet in fluid communication with the desolvation region, for receiving the desolvated sample ions along with solvent vapors comprising non-ionized solvent and solvent ions, the separation chamber having electrodes separated by a gap for generating an electric field within the separation chamber, the electric field defines a first curved flow path for sample ions from the separation chamber inlet through the gap to a separation chamber outlet, but which causes unwanted solvent ions and unwanted non-ionized solvent vapors to be directed away from the separation chamber outlet; and
   a reaction chamber having an inlet in fluid communication with the separation chamber outlet, for receiving the sample ions from the separation chamber and for decomposing the received ions into smaller products.

2. The sample introduction system of claim 1, wherein ions and non-ionized solvent enter the separation chamber through the separation chamber inlet in a first direction defining a first axis, and wherein sample ions following the first flow path exit the separation chamber through the separation chamber outlet in a second direction defining a second axis, and wherein the first and second axes are not coincident.

3. The sample introduction system in accordance with claim 1, wherein the separation chamber further comprises a gas supply for supplying a flow of gas in a direction transverse or counter to the direction of travel of ions as they enter the separation chamber through the separation chamber inlet, so as to cause sample ions, having a first ion mobility or range of ion mobilities, to be directed along the said first flow path towards the separation chamber outlet, but to cause unwanted solvent ions, having a second ion mobility or range of ion mobilities different to the said first ion mobility or range of mobilities, and unwanted non-ionized solvent, to be directed along one or more further flow paths away from the separation chamber outlet.

4. The sample introduction system in accordance with claim 2, wherein the first and second axes are substantially parallel but offset from one another.

5. The sample introduction system in accordance with claim 1, wherein the electrodes of the separation chamber comprise a first electrode arrangement arranged to generate a DC and/or an AC electric field, so as to cause sample ions, having a first mass to charge ratio or range of mass to charge ratios, to be directed along the said first flow path towards the separation chamber outlet, but to cause unwanted solvent ions, having a second mass to charge ratio or range of mass to charge ratios, different to the said first mass to charge ratio or range of ratios, and unwanted non-ionized solvent to be directed away from the separation chamber outlet.

6. The sample introduction system of claim 5, wherein the solvent ions have a higher or lower mass to charge ratio or range of mass to charge ratios than that or those of the sample ions, the DC and/or AC component of the first electrode arrangement guiding the said sample ions toward the separation chamber outlet whilst dispersing the said relatively heavier or lighter solvent ions.

7. The sample introduction system of claim 5, wherein the said first electrode arrangement of the separation chamber cause the said sample ions to be guided along a curved flow path defining the said first flow path, and further wherein the first axis is substantially perpendicular to the said second axis.

8. The sample introduction system of claim 5, wherein the first electrode arrangement is arranged to generate an asymmetric AC electric field so as to cause unwanted solvent ions to be dispersed within the separation chamber whilst sample ions are directed toward the separation chamber outlet.

9. The sample introduction system of claim 2, wherein the electrodes of the separation region comprise a first electrode arrangement arranged to generate both a DC and an AC electric field and further comprise a second electrode arrangement arranged to generate a DC electric field that accelerates ions in a direction having a component perpendicular to the said first direction defining the said first axis so as to be directed by the first electrode arrangement along the said first flow path towards the separation chamber outlet, but to cause unwanted solvent ions, having a second mass to charge ratio or range of mass to charge ratios, different to the said first mass to charge ratio or range of ratios, and unwanted non-ionized solvent to be directed away from the separation chamber outlet.

10. The sample introduction system of claim 9, further comprising a power supply arranged to supply AC and/or DC voltages to the electrodes, wherein the power supply is configured to supply a first DC voltage to the second electrode arrangement so as to deflect sample ions away from the first direction defining the first axis, wherein the power supply is configured to supply a second DC voltage to the first electrode arrangement so as to accelerate sample ions in a direction having a component perpendicular with the said first axis, and further wherein the power supply is configured to apply an AC voltage to the first electrode arrangement at a frequency that guides the sample ions into the separation chamber outlet.

11. The sample introduction system of claim 1, further comprising a liquid separator upstream of the desolvation region for separating one or more components of the sample in the solvent matrix, and an ionization source for receiving the said separated sample from the liquid separator and ionizing it so as to produce the said sample ions in the solvent matrix.

12. The sample introduction system of claim 11, wherein the ionization source is positioned in the desolvation region, upstream of, and spatially separated from, the separation region inlet.

13. The sample introduction system of claim 1, wherein the desolvation region further includes a heated channel positioned therein, at or adjacent to the separation chamber inlet.

14. The sample introduction system of claim 13, wherein the heated channel is extended in one dimension to increase transmitted ion current without compromising desolvation.

15. The sample introduction system of claim 13, wherein a single ionization source or array of ionization sources is extended along the extension of the heated channel.

16. The sample introduction system of claim 1, wherein the desolvation region is formed within a desolvation chamber, the sample introduction system further comprising a heated gas supply connected to the desolvation chamber for supply of a heated gas thereto.

17. The sample introduction system of claim 1, wherein the desolvation region is formed within a desolvation chamber, the sample introduction system further comprising a pumping arrangement connected to the desolvation chamber for adjusting the pressure within the desolvation chamber.

18. The sample introduction system of claim 17, wherein the pumping arrangement is further connected to the separation chamber for adjusting the pressure therein.

19. The sample introduction system of claim 18, further comprising a pumping controller for controlling the pumping arrangement so that the pressure, $P_{sampling}$, within the desolvation chamber, is at least twice the pressure, $P_{sep}$, in the separation chamber.

20. The sample introduction system of claim 1, wherein the reaction chamber is at atmospheric pressure in use.

21. The sample introduction system of claim 17, wherein the pumping arrangement is further connected to the reaction chamber, the system further comprising a pumping controller for controlling the pumping arrangement so as maintain the pressure in the reaction chamber between around 50 kPa (0.5 Atm) and 200 kPa (2 Atm).

22. The sample introduction system of claim 1, further comprising a counter gas supply for supplying counter gas to the separation chamber outlet, the counter gas being caused to flow in a direction generally opposed to the direction of incidence of the sample ions thereat.

23. The sample introduction system of claim 1, further comprising a $CO_2$ separation unit downstream of the reaction chamber.

24. The sample introduction system of claim 1, wherein the reaction chamber comprises a combustion chamber or an oxidation or pyrolysis chamber.

25. The sample introduction system of claim 24, wherein the oxidation or pyrolysis chamber is positioned upstream or downstream of the combustion chamber.

26. The sample introduction system of claim 24, further comprising a valve positioned downstream of the separation chamber outlet, the valve being configurable, in a first valve position, to direct sample ions exiting the separation chamber outlet toward the combustion chamber, and in a second valve position, to direct sample ions exiting the separation chamber outlet toward the oxidation or pyrolysis chamber.

27. An Isotope Ratio Mass Spectrometer (IRMS) including the sample introduction system of claim 1.

* * * * *